US006869620B2

(12) United States Patent
Moore, Jr.

(10) Patent No.: US 6,869,620 B2
(45) Date of Patent: Mar. 22, 2005

(54) PRODUCTION OF CONCENTRATED BIOCIDAL SOLUTIONS

(75) Inventor: Robert M. Moore, Jr., Baton Rouge, LA (US)

(73) Assignee: Albemarle Corporation, Richmond, CA (US)

( * ) Notice: Subject to any disclaimer, the term of this patent is extended or adjusted under 35 U.S.C. 154(b) by 0 days.

(21) Appl. No.: 10/370,333

(22) Filed: Feb. 18, 2003

(65) Prior Publication Data

US 2003/0124203 A1 Jul. 3, 2003

Related U.S. Application Data

(60) Continuation of application No. 10/120,334, filed on Apr. 10, 2002, now Pat. No. 6,551,624, which is a division of application No. 09/658,839, filed on Sep. 8, 2000, now Pat. No. 6,375,991.

(51) Int. Cl.$^7$ .......................... A01N 59/02; A01N 59/00
(52) U.S. Cl. ...................................... 424/703; 424/723
(58) Field of Search ................................ 424/703, 723

(56) References Cited

U.S. PATENT DOCUMENTS

| | | | |
|---|---|---|---|
| 3,152,073 A | 10/1964 | Morton ......................... 210/62 |
| 3,170,883 A | 2/1965 | Owen et al. .................. 252/187 |
| 3,222,276 A | 12/1965 | Belohlav et al. |
| 3,308,062 A | 3/1967 | Gunther ........................ 210/58 |
| 3,328,294 A | 6/1967 | Self et al. ..................... 210/62 |
| 3,558,503 A | 1/1971 | Goodenough et al. ...... 252/187 |
| 3,589,859 A | 6/1971 | Foroulis ........................ 21/2.7 |
| 3,711,246 A | 1/1973 | Foroulis ........................ 21/2.7 |
| 3,749,672 A | 7/1973 | Golton et al. .................. 252/95 |
| 3,767,586 A | 10/1973 | Rutkiewic .............. 252/187 H |
| 4,032,460 A | 6/1977 | Zilch et al. ............. 252/8.55 B |
| 4,237,090 A | 12/1980 | DeMonbrun et al. ......... 422/13 |
| 4,295,932 A | 10/1981 | Pocius ......................... 162/161 |
| 4,382,799 A | 5/1983 | Davis et al. .................... 8/107 |
| 4,427,435 A | 1/1984 | Lorenz et al. .................. 71/67 |
| 4,451,376 A | 5/1984 | Sharp .......................... 210/701 |
| 4,465,598 A | 8/1984 | Darlington et al. ......... 210/721 |
| 4,476,930 A | 10/1984 | Watanabe .................... 166/279 |
| 4,490,308 A | 12/1984 | Fong et al. ............. 260/513 N |
| 4,539,071 A | 9/1985 | Clifford et al. ............. 162/161 |
| 4,546,156 A | 10/1985 | Fong et al. .................. 526/240 |
| 4,566,973 A | 1/1986 | Masler, III et al. ......... 210/701 |
| 4,595,517 A | 6/1986 | Abadi .......................... 252/82 |
| 4,595,691 A | 6/1986 | LaMarre et al. ............. 514/367 |
| 4,604,431 A | 8/1986 | Fong et al. .................. 525/351 |
| 4,642,194 A | 2/1987 | Johnson ....................... 210/699 |
| 4,643,835 A | 2/1987 | Koeplin-Gall et al. ...... 210/754 |
| 4,661,503 A | 4/1987 | Martin et al. ................ 514/372 |
| 4,680,339 A | 7/1987 | Fong .......................... 525/54.11 |
| 4,680,399 A | 7/1987 | Buchardt ..................... 546/139 |
| 4,703,092 A | 10/1987 | Fong .......................... 525/351 |
| 4,711,724 A | 12/1987 | Johnson ....................... 210/699 |
| 4,752,443 A | 6/1988 | Hoots et al. .................. 422/13 |
| 4,759,852 A | 7/1988 | Trulear ....................... 210/699 |
| 4,762,894 A | 8/1988 | Fong et al. .................. 525/344 |
| 4,777,219 A | 10/1988 | Fong ........................ 525/329.4 |
| 4,801,388 A | 1/1989 | Fong et al. .................. 210/701 |
| 4,802,990 A | 2/1989 | Inskeep, Jr. ................. 210/699 |
| 4,822,513 A | 4/1989 | Corby ......................... 252/106 |
| 4,846,979 A | 7/1989 | Hamilton .................... 210/754 |
| 4,883,600 A | 11/1989 | MacDonald et al. ........ 210/696 |
| 4,886,915 A | 12/1989 | Favstritsky .................. 564/503 |
| 4,898,686 A | 2/1990 | Johnson et al. ........... 252/389.2 |
| 4,906,651 A | 3/1990 | Hsu ............................. 514/372 |
| 4,923,634 A | 5/1990 | Hoots et al. ............. 252/389.2 |
| 4,929,424 A | 5/1990 | Meier et al. .................... 422/9 |
| 4,929,425 A | 5/1990 | Hoots et al. .................. 422/13 |
| 4,966,716 A | 10/1990 | Favstritsky et al. ......... 210/755 |
| 4,992,209 A | 2/1991 | Smyk et al. ................. 252/387 |
| 4,995,987 A | 2/1991 | Whitekettle et al. ........ 210/754 |
| 5,034,155 A | 7/1991 | Soeder et al. ........... 252/389.23 |
| 5,035,806 A | 7/1991 | Fong et al. .................. 210/701 |

(List continued on next page.)

FOREIGN PATENT DOCUMENTS

| GB | 2302687 | 1/1997 |
|---|---|---|
| WO | 9015780 | 12/1990 |
| WO | WO 96/30562 | 10/1996 |
| WO | 9720546 | 6/1997 |
| WO | 9720909 | 6/1997 |
| WO | 9734827 | 9/1997 |
| WO | 9743392 | 11/1997 |
| WO | 9815609 | 4/1998 |
| WO | 9906320 | 2/1999 |
| WO | 9932596 | 7/1999 |
| WO | 9955627 | 11/1999 |
| WO | 9962339 | 12/1999 |
| WO | 0058532 | 10/2000 |

OTHER PUBLICATIONS

Ault et al., "Infrared and Raman Spectra of the M+Cl$_3$–ion Pairs and Their Chlorine–bromine Counterparts isolated in Argon Matrices", Journal of Chemical Physics, 1976, vol. 64, No. 12, pp. 4853–4859.

Willard et al.; "Elementary Quantitative Analysis," Third Edition, Chapter XIV—"Oxidation and Reduction Processes Involving Iodine (Iodometry)," 1940 p. 261–271.

Affidavit of Shunong Yang, William F. McCoy and Anthony W. Dallmier, Under 37 C.F.R. §1.13; presumably made public on Sep. 11, 2001, 13–pages. This Affidavit is contained in the File Wrapper of U.S. Appl. No. 09/518,435 now US 6,287,473, issued Sep. 11, 2001.

*Primary Examiner*—Alton N. Pryor
(74) *Attorney, Agent, or Firm*—Edgar E. Spielman, Jr.

(57) ABSTRACT

The production process comprises A) forming an acidic aqueous solution comprising alkali metal cations, bromide anions, and sulfamate anions; B) feeding into said aqueous solution a source of alkali metal cations and chlorine-containing bromide oxidant proportioned to keep the resultant aqueous medium acidic and to form an acidic product solution containing at least about 5 wt % of active bromine, and C) raising the pH of the aqueous product solution with water-soluble base to at least about 10.

6 Claims, No Drawings

U.S. PATENT DOCUMENTS

| | | | |
|---|---|---|---|
| 5,047,164 A | 9/1991 | Corby | 252/106 |
| 5,055,285 A | 10/1991 | Duncan et al. | 423/473 |
| 5,118,426 A | 6/1992 | Duncan et al. | 210/721 |
| 5,120,452 A | 6/1992 | Ness et al. | 210/754 |
| 5,120,797 A | 6/1992 | Fong et al. | 525/329.4 |
| 5,141,652 A | 8/1992 | Moore, Jr. et al. | 210/754 |
| 5,179,173 A | 1/1993 | Fong et al. | 525/329.4 |
| 5,192,459 A | 3/1993 | Tell et al. | 252/106 |
| 5,194,238 A | 3/1993 | Duncan et al. | 423/473 |
| 5,196,126 A | 3/1993 | O'Dowd | 210/754 |
| 5,202,047 A | 4/1993 | Corby | 252/106 |
| 5,259,985 A | 11/1993 | Nakanishi et al. | 252/180 |
| 5,264,136 A | 11/1993 | Howarth et al. | 210/754 |
| 5,389,384 A | 2/1995 | Jooste | 424/661 |
| 5,414,652 A | 5/1995 | Mieda et al. | 365/122 |
| 5,424,032 A | 6/1995 | Christensen et al. | 422/14 |
| 5,443,849 A | 8/1995 | Corby | 424/667 |
| 5,464,636 A | 11/1995 | Hight et al. | 424/661 |
| 5,525,241 A | 6/1996 | Clavin et al. | 210/753 |
| 5,527,547 A | 6/1996 | Hight et al. | 424/661 |
| 5,589,106 A | 12/1996 | Shim et al. | 252/387 |
| 5,607,619 A | 3/1997 | Dadgar et al. | 252/187.2 |
| 5,679,239 A | 10/1997 | Blum et al. | 205/556 |
| 5,683,654 A | 11/1997 | Dallmier et al. | 422/14 |
| 5,795,487 A | 8/1998 | Dallimier et al. | 210/754 |
| 5,922,745 A | 7/1999 | McCarthy et al. | 514/372 |
| 5,942,126 A | 8/1999 | Dallmier et al. | 210/756 |
| 6,007,726 A | 12/1999 | Yang et al. | 210/752 |
| 6,037,318 A * | 3/2000 | Na et al. | 510/379 |
| 6,068,861 A | 5/2000 | Moore, Jr. et al. | 424/703 |
| 6,110,387 A | 8/2000 | Choudhury | 210/752 |
| 6,123,870 A | 9/2000 | Yang et al. | 252/186.1 |

\* cited by examiner

PRODUCTION OF CONCENTRATED BIOCIDAL SOLUTIONS

REFERENCE TO RELATED APPLICATIONS

This case is a continuation of commonly-owned application Ser. No. 10/120,334, filed Apr. 10, 2002, now U.S. Pat. No. 6,551,624, which in turn is a division of commonly-owned application Ser. No. 09/658,839, filed Sep. 8, 2000, now U.S. Pat. No. 6,375,991 B1, issued Apr. 23, 2002.

REFERENCE TO COMMONLY-OWNED PATENT AND COPENDING PATENT APPLICATIONS

The following commonly-owned copending U.S. patent applications relate to concentrated aqueous bromine- and sulfamate-containing biocidal solutions, processes for production of such solutions, and/or methods of using such solutions in water treatment or in control of biofilms:

U.S. Pat. No. 6,068,861 issued May 30, 2000, based on application Ser. No. 09/088,300, filed Jun. 1, 1998, and a Continued Prosecution Application (CPA) thereof.

Application Ser. No. 09/404,184, filed Sep. 24, 1999, now U.S. Pat. No. 6,322,822, issued Nov. 27, 2001, which is a continuation-in-part of application Ser. No. 09/088,300.

Application Ser. No. 09/442,025, filed Nov. 17, 1999, now U.S. Pat. No. 6,306,441, issued Oct. 23, 2001, which is a continuation-in-part of application Ser. No. 09/088,300.

Application Ser. No. 09/451,319, filed Nov. 30, 1999, which is a continuation-in-part of application Ser. No. 09/088,300.

Application Ser. No. 09/451,344, filed Nov. 30, 1999, which is a continuation-in-part of application Ser. No. 09/442,025, filed Nov. 17, 1999, which is a continuation-in-part application Ser. No. 09/088,300.

Application Ser. No. 09/456,781, filed Dec. 8, 1999, which is a continuation of application Ser. No. 09/088,300.

Application Ser. No. 09/506,911, filed Feb. 18, 2000, which is a continuation-in-part of application Ser. No. 09/088,300, and a continuation-in-part of application Ser. No. 09/404,184.

Application Ser. No. 09/296,499, filed Apr. 22, 1999, now U.S. Pat. No. 6,110,387, issued Aug. 29, 2000.

BACKGROUND

Bromine-based biocides have proven biocidal advantages over chlorination-dechlorination for the microbiological control of cooling waters and disinfection of waste treatment systems. The water treatment industry recognizes these advantages to be cost-effective control at higher pH values, almost no loss in biocidal activity in the presence of ammonia, and effective control of bacteria, algae and mollusks.

A common way of introducing bromine based biocides into a water system is through the use of aqueous NaBr in conjunction with NaOCl bleach. The user feeds both materials to a common point whereupon the NaOCl oxidizes the bromide ion to $HOBr/OBr^{\ominus}$. This activated solution is then introduced directly into the water system to be treated. The feeding of the two liquids in this fashion is necessary because the $HOBr/OBr^{\ominus}$ mixture is unstable and has to be generated on-site just prior to its introduction to the water. Furthermore, the feeding, and metering of two liquids is cumbersome, especially as the system has to be designed to allow time for the activation of bromide ion to occur.

Consequently many biocide users have expressed the need for a single-feed, bromine-based biocide. Elemental bromine and molecular bromine chloride have been considered to meet these demands. Both are liquids at room temperature and can be fed directly to the water system, where immediate hydrolysis occurs to yield HOBr.

$$Br_2 + H_2O \rightarrow HOBr + HBr \qquad (1)$$

$$BrCl + H_2O \rightarrow HOBr + HCl \qquad (2)$$

Properties of bromine and bromine chloride are compared in Table 1.

TABLE 1

Physical Properties of Bromine and Bromine Chloride

| Property | Bromine ($Br_2$) | Bromine Chloride (BrCl) |
|---|---|---|
| Appearance | Fuming, dark-red liquid | Fuming, red liquid or gas |
| Boiling Point | 59° C. | 5° C. |
| Vapor Pressure (25° C.) | 214 mm | 1800 mm |
| Corrosivity | Corrodes most metals in the presence of water | Corrodes most metals in the presence of water |

It can be seen that certain characteristics of these materials—especially their corrosiveness, high vapor pressures and fuming tendencies—necessitate care and skill in their handling and use. Early efforts to overcome the deficiencies of these materials comprised complexing bromine with excess bromide ion in the presence of strong acid and stabilizing the resultant solutions with ethanolamine. The resultant solutions of ethanolammonium hydrogen perbromide contained up to 38% by weight elemental bromine. See in this connection, Favstritsky, U.S. Pat. No. 4,886,915; and Favstritsky, Hein, and Squires, U.S. Pat. No. 4,966,716.

These solutions permitted introduction of bromine to a water system using a single feed. As in the case of bromine and bromine chloride, the ethanolammonium hydrogen perbromide hydrolyzed in water to release HOBr. The vapor pressures of these solutions were lower than elemental bromine and bromine chloride. Nevertheless, the solutions still possessed measurable vapor pressures, and thus tended to produce undesirable reddish-colored vapors during storage and use.

An economically acceptable way of stabilizing high concentrations of aqueous solutions of bromine chloride is described in U.S. Pat. No. 5,141,652 to Moore, et al. The solution is prepared from bromine chloride, water and a halide salt or hydrohalic acid. These solutions were found to decompose at a rate of less than 30% per year and in cases of high halide salt concentration, less than 5% per year. Moreover, solutions containing the equivalent of 15% elemental bromine could be prepared. Unfortunately, the relatively high acidity of these solutions and their tendency to be corrosive and fuming impose limitations on their commercial acceptance.

Many solid bromine derivatives such as BCDMH (1,3-bromochloro-5,5-dimethylhy-dantoin) are limited in the amount of material that can be dissolved in water and fed as a liquid to the water treatment system. For example, the solubility of BCDMH in water is only around 0.15%. Another limitation of such derivatives is that at neutral pH, HOBr rapidly decomposes, eventually forming bromide ions. Thus, the ability to store and transport these aqueous solutions is greatly limited and of questionable commercial feasibility.

U.S. Pat. No. 3,558,503 to Goodenough et al. describes certain aqueous bromine solutions stabilized with various stabilizing agents and various uses to which such solutions can be put. The compositions described in the patent comprise an aqueous bromine solution having from about 0.01 to about 100,000 parts per million by weight of bromine values wherein the molar ratio of bromine to nitrogen present in the bromine stabilizer ranges from about 2.0 to 1 to about 0.5 to 1. The stabilizer used is biuret, succinimide, urea, a lower aliphatic mono- or disubstituted urea containing from about 2 to about 4 carbon atoms in each substituent group, sulfamic acid, or an alkyl sulfonamide of the formula $RSO_3NH_2$ where R is a methyl or ethyl group. The solution also contains sufficient hydroxide additive to provide a pH in the solution ranging from about 8 to about 10, the hydroxide additive being an alkaline earth hydroxide or an alkali metal hydroxide.

U.S. Pat. No. 5,683,654 to Dallmier et al. discusses the preparation of aqueous alkali metal or alkaline earth metal hypobromite solutions by mixing an aqueous solution of alkali or alkaline earth metal hypochlorite with a water soluble bromide ion source to form a solution of unstabilized alkali or alkaline earth metal hypochlorite. To this solution is added an aqueous solution of an alkali metal sulfamate having a temperature of at least 50° C. and in an amount that provides a molar ratio of alkali metal sulfamate to alkali or alkaline earth metal hypobromite of from about 0.5 to about 6 whereby a stabilized aqueous alkali or alkaline earth metal hypobromite solution is formed. The Dallmier et al. patent teaches that much higher levels of available halogen for disinfection were attained by this approach as compared to the Goodenough et al. approach. But the Dallmier et al. patent acknowledges that in their process, the stabilization must occur quickly after the unstable NaOBr is formed.

U.S. Pat. No. 5,795,487 to Dallmier et al. describes a method for preparing a stabilized alkali or alkaline earth metal hypobromite solution. The method comprises mixing an aqueous solution of alkali or alkaline earth metal hypochlorite having about 5–70% of available halogen as chlorine with a water-soluble bromide ion source, allowing the bromide ion source and the hypochlorite to react to form a 0.5–70 wt % aqueous solution of unstabilized alkali or alkaline earth metal hypobromite, adding to this unstabilized solution an aqueous solution of an alkali metal sulfamate in amount to provide a molar ratio of alkali metal sulfamate to alkali or alkaline earth metal hypobromite of from about 0.5 to about 0.7, and recovering a stabilized aqueous alkali or alkaline earth metal hypobromite solution. The order of addition in the process is said to be critical.

U.S. Pat. No. 6,007,726 to Yang et al. describes the formation of stabilized bromine formulations. In that process, a solution of alkali or alkaline earth metal bromide and an halogen stabilizer such as sulfamic acid is formed and adjusted to a pH of about 4 to about 8. To this solution is added ozone, a peroxide, or a peracid such as peracetic acid, to generate an oxidizing bromine compound in the solution. The pH of the solution can then be raised to 13 or above. The process is demonstrated by use of ozone from an ozonator, and it is indicated that it is important to maintain a high reaction pH and a low reaction temperature to keep the stable oxidizing bromines from thermally decomposing.

BRIEF SUMMARY OF THE INVENTION

This invention involves a new process of forming concentrated aqueous solutions of biocidally active bromine and in so doing, provides novel concentrated aqueous solutions which are useful precursors or intermediates for the production of biocidal solutions containing active bromine. Such concentrated biocidal solutions can be stored and shipped, and they can serve as articles of commerce which, in use, are mixed into the water to be treated for microbiological control. The concentrated aqueous biocidal solutions are also useful in combating biofilms on surfaces contacted by water. Thus when put to use for microbiological control or biofilm eradication, the concentrated biocidal solutions are normally diluted in the water being treated. However, in severe cases it is possible to apply a concentrated solution or a partially diluted concentrated solution directly onto a surface infested with biofilm and/or other microbial species or pathogens.

In one of its embodiments this invention provides a process of producing a concentrated liquid biocide composition, which process comprises:

A) forming an acidic aqueous solution, preferably an acidic solution in which the pH is at least about 1 (i.e., the numerical value of the pH of the acidic solution is about 1 or above, but of course is less than 7), comprising alkali metal cations, bromide anions, and sulfamate anions;

B) feeding into said aqueous solution a source of alkali metal cations and chlorine-containing bromide oxidant proportioned to keep the resultant aqueous medium acidic and to form an acidic product solution containing at least about 5 wt % of active bromine; and C) raising the pH of the aqueous product solution with water-soluble base to at least about 10, preferably using at least one water-soluble alkali metal base.

It will be seen that the reaction that produces the active bromine is performed in an acidic aqueous reaction medium and thereby forms the product solution of B) above. This solution serves as a precursor or intermediate composition from which the concentrated liquid biocide composition is formed in C) above. Despite the high concentration of active bromine in the acidic product solution of B) above, this acidic solution is sufficiently stable to be useful in forming the more stable alkaline concentrated liquid biocide composition of C) above.

Thus another embodiment of this invention is an acidic aqueous solution containing sulfamate and at least about 10 wt % of active bromine. Such solution is best produced by forming an acidic aqueous solution, preferably having a pH of at least about 1, comprising alkali metal cations, bromide anions, and sulfamate anions; and feeding into such aqueous solution a source of alkali metal cations and chlorine-containing bromide oxidant proportioned to keep the resultant aqueous medium acidic (i.e., to keep the pH below 7) and to form an acidic product solution containing at least about 5 wt % of active bromine.

A feature of this invention is that it makes possible the formation of concentrated aqueous active bromine-containing solutions having any of a variety of desirable atom ratios of nitrogen to active bromine derived from the bromide and sulfamate anions. Typically, such ratio should be greater than about 0.93:1, and preferably greater than 1:1. In fact, it is possible to form a concentrated aqueous biocide solution having an atom ratio of nitrogen to active bromine as high as about 1.5:1 or more. Such high ratios ensure the presence in the concentrated aqueous biocide solution of a substantial excess of sulfamate anions. This in turn ensures that the solution will retain its excellent stability over long periods of time.

Another feature of this invention is that the concentrated aqueous biocide compositions are not produced by use of powerful oxidants such as ozone, peroxides, or other peroxygen compounds which are known to possess undesirable, and indeed, hazardous characteristics. Indeed, a preferred chlorine-containing bromide oxidant in the process of this invention is chlorine. Consequently, from the inception of their production, the concentrated aqueous biocide compositions produced in a process of this invention are and remain at all times free of added ozone, peroxide, or other peroxygen compound.

The above and other features and embodiments of this invention will be still further apparent from the ensuing description and appended claims.

FURTHER DETAILED DESCRIPTION

As noted above, the process of this invention involves reaction in an acidic aqueous medium followed by increase of the pH to at least about 10. The acidic aqueous medium is desirably kept at a pH in the range of about 1 to about 6, and more preferably in the range of about 2 to about 5. It is to be emphasized and clearly understood that pH excursions out of these ranges for one or more brief periods during the process can be tolerated and are within the contemplation and scope of this invention provided that the concentrated aqueous biocide solution produced from these components has an active bromine content of at least about 5 wt %, preferably at least about 7 wt %, and more preferably at least about 10 wt %.

Inasmuch as the process of this invention is performed in an aqueous medium, a variety of different sources of alkali metal cations, bromide anions and sulfamate anions are available for use. The chief requirements are that the source be sufficiently water soluble to provide the requisite quantities of these cations and anions in the reaction medium, and that the sources are free of constituents that would materially interfere with the conduct of the process. Examples of such sources include alkali metal bromides (typically LiBr, NaBr, and/or KBr), alkaline earth metal bromides (typically $MgBr_2$ and/or $CaBr_2$), alkali metal hydroxides or oxides (typically NaOH, $Na_2O$, KOH, and/or $K_2O$), alkali metal sulfamates (typically sodium sulfamate and/or potassium sulfamate), and similar substances. Although the solubility of sulfamic acid in water is relatively low, because the solution formed in A) above contains alkali metal cations, the equilibrated mixture when using sulfamic acid results in an ample quantity of dissolved sulfamate anions.

As noted above, chlorine is a preferred chlorine-containing bromide oxidant in the process. By "chlorine-containing bromide oxidant" is meant either (a) chlorine itself (which of course has the capability of oxidizing bromide), or (b) a compound capable of oxidizing a bromide and containing at least one chlorine atom in the molecule. The interaction between the bromide anions and the chlorine-containing bromide oxidant results in the formation of the active bromine species in the reaction mixture.

Use of an alkali metal bromide and chlorine in the process results in the co-production of alkali metal chloride, which lowers the freezing point of the resultant concentrated aqueous solution, a feature which is desirable in the case of outdoor storage during cold weather.

To raise the pH of the aqueous solution in C), it is desirable to employ one or more basic sources of alkali metal cations. Typically, the alkali metal base used in the practice of this invention is any water-soluble basic inorganic alkali metal compound or any sparingly soluble basic inorganic alkali metal compound which interacts with water to form water-soluble alkali metal species, normally cations.

Suitable inorganic alkali metal bases include the carbonates, bicarbonates, oxides, hydroxides, amides, hydrides, and alcoholates, ROM, where R is a hydrocarbyl group such as alkyl, alkenyl, cycloalkyl, cycloalkenyl, aryl, aralkyl, and the like, and M is an alkali metal atom, viz., Li, Na, K, Rb, or Cs. The oxides are preferred. The hydroxides are particularly preferred. Of the alkali metal compounds, Cs and especially Rb compounds are quite expensive, whereas Li compounds are more abundant and usually less expensive than corresponding Rb and Cs compounds. Compounds in which the alkali metal is K are preferred, and compounds of Na are most preferred, because of their greater availability and superior cost-effectiveness. Thus use of oxides or hydroxides of potassium or sodium is preferred, with sodium oxide or hydroxide being more preferred, and NaOH being most preferred.

While any water-soluble salt of sulfamic acid could be used as the source of sulfamate anions, for the purposes of water treatment, the nature of the cation should be taken into consideration. Thus, for this use, alkali metal salts of sulfamic acid, such as lithium sulfamate, sodium sulfamate, and potassium sulfamate are materials of choice. Of these, potassium sulfamate is preferred. Sodium sulfamate is particularly preferred. The alkali metal sulfamate can be preformed but preferably is formed in situ by interaction between sulfamic acid and an alkali metal base such as sodium hydroxide. In the case of biofilm eradication on surfaces periodically or continuously in contact with cooling water, e.g., in cooling towers, it is possible to have cations in the solution other than alkali metal cations. Such other cations can be the ammonium cation, alkaline earth cations, e.g., calcium or magnesium, or cations of certain heavy metals, e.g., iron or manganese. However, even in such biofilm eradication, the presence of alkali metal cations in lieu of other cations is definitely preferable.

Generally speaking, the temperature of the reaction mixture is preferably not above about 50° C., and thus is typically in the range of about 10 to about 50° C., and more preferably is in the range of about 20 to about 40° C. However, suitable departures from these temperature ranges are permissible and within the scope of this invention whenever deemed necessary or desirable, provided that neither the conduct of the process nor the character of the product is adversely affected in a material manner.

Produced by the process of this invention is a storage-stable concentrated liquid biocide composition which comprises water having in solution therein (i) an active bromine content of at least about 5 wt %, preferably at least about 7 wt %, and more preferably at least about 10 wt %, (ii) a sulfamate content, (iii) a chloride content, and (iv) a pH of at least about 10, preferably at least about 10.8, e.g., a pH of at least about 12, and more preferably at least about 13. The higher the pH of these solutions, the more stable the composition. Typically, the sulfamate content is such that the atom ratio of nitrogen to active bromine is greater than about 0.93:1, preferably greater than 1:1, and even as high as about 1.5:1 or more. In addition, the concentrated liquid biocide composition will contain one or more water-soluble cation species derived from components used in the production process.

When the concentrated basic aqueous solution formed pursuant to this invention is to be stored in steel drums, it is desirable to have the pH of such solution at about 10 or above, and preferably at least about 12, and more preferably at least about 13, e.g., in the range of about 12.5 to about 13.5.

Another embodiment of this invention is a concentrated acidic composition useful as a precursor in the production of the above concentrated liquid biocide compositions. This acidic composition comprises water having in solution therein (i) an active bromine content of at least about 5 wt % (50,000 ppm, wt/wt), preferably at least about 7 wt %, and more preferably at least about 10 wt %, (ii) a sulfamate content, and (iii) a chloride content, and in addition, the solution has a pH of below 7, e.g., a pH in the range of about 1 to about 6, and preferably in the range of about 1.5 to about 4.5. Typically, the sulfamate content is such that it provides an atom ratio of nitrogen to active bromine greater than about 0.93:1, preferably greater than 1:1, and even as high as about 1.5:1 or more. These solutions, although much less stable than the above concentrated liquid biocide solutions, are nevertheless stable enough to be prepared and used in the production of the above concentrated liquid biocide solutions. Thus the concentrated acidic compositions of this invention are useful, discrete compositions which exist as such until the pH of the solution is raised. In addition, the acidic composition normally contains one or more water-soluble cationic species derived from one or more water-soluble components used in the process.

The term "active bromine" of course refers to all bromine-containing species that are capable of biocidal activity. It is generally accepted in the art that all of the bromine in the +1 oxidation state is biocidally active and is thus included in the term "active bromine". As is well known in the art, bromine, bromine chloride, hypobromous acid, hypobromite ion, hydrogen tribromide, tribromide ion, and organo-N-brominated compounds have bromine in the +1 oxidation state. Thus these, as well as other such species to the extent they are present, constitute the active bromine content of the compositions of this invention. See, for example, U.S. Pat. Nos. 4,382,799 and 5,679,239. A well-established method in the art for determining the amount of active bromine in a solution is starch-iodine titration, which determines all of the active bromine in a sample, regardless of what species may constitute the active bromine. The usefulness and accuracy of the classical starch-iodine method for quantitative determination of bromine and many other oxidizing agents has long been known, as witness Chapter XIV of Willard-Furman, *Elementary Quantitative Analysis*, Third Edition, D. Van Nostrand Company, Inc., New York, Copyright 1933, 1935, 1940.

A typical starch-iodine titration to determine active bromine is carried out as follows: A magnetic stirrer and 50 milliliters of glacial acetic acid are placed in an iodine flask. The sample (usually about 0.2–0.5 g) for which the active bromine is to be determined is weighed and added to the flask containing the acetic acid. Water (50 milliliters) and aqueous potassium iodide (15% (wt/wt); 25 milliliters) are then added to the flask. The flask is stoppered using a water seal. The solution is then stirred for fifteen minutes, after which the flask is unstoppered and the stopper and seal area are rinsed into the flask with water. An automatic buret (Metrohm Limited) is filled with 0.1 normal sodium thiosulfate. The solution in the iodine flask is titrated with the 0.1 normal sodium thiosulfate; when a faint yellow color is observed, one milliliter of a 1 wt % starch solution in water is added, changing the color of the solution in the flask from faint yellow to blue. Filtration with sodium thiosulfate continues until the blue color disappears. The amount of active bromine is calculated using the weight of the sample and the volume of sodium thiosulfate solution titrated. Thus, the amount of active bromine in a composition of this invention, regardless of actual chemical form, can be quantitatively determined.

A common variant in the above typical starch-iodine titration is the use of sodium arsenite in place of sodium thiosulfate. This procedure is also referred to in Chapter XIV of Willard-Furman, *Elementary Quantitative Analysis*, Third Edition, cited above. See also Farkas and Lewin, *Analytical Chem.*, 1947, 19, 662–664.

When used for microbiological control, the concentrated basic solutions produced in a process of this invention are mixed or diluted with, or introduced into, additional water, which typically is the water being treated for microbiological control, so that the amount of active bromine in the water being treated for microbiological control is a microbiologically effective amount. In general, a microbiologically effective amount on a wt/wt basis in the treated water is typically in the range of about 0.5 to about 20 parts per million of bromine (expressed as $Br_2$) and preferably in the range of about 4 to about 10 parts per million of bromine (expressed as $Br_2$) in the aqueous medium being treated for biocidal and/or biofilm control. Such dosages will usually suffice. However, higher dosages can be used whenever deemed necessary or desirable. The various concentrated biocide solutions produced pursuant to this invention preferably, and in most cases, additionally contain dissolved chloride ion, most preferably in the presence of a stoichiometric excess relative to chloride anion, of alkali metal cation, such as sodium or potassium cations. Alkali metal chloride salts have high solubilities in the aqueous medium of the concentrates formed using a process of this invention, and thus pose no problem with respect to precipitate formation during storage, transportation, or use. In addition, the dissolved alkali metal chloride in the concentrated aqueous solutions produced pursuant to this invention should minimize the extent to which oxygen or air becomes dissolved in the solution, and also reduce the freezing point of the solution.

This invention has made it possible to produce an aqueous biocide composition that (a) is devoid or essentially devoid of bromate, and (b) since its inception has been devoid or essentially devoid of bromate. By "devoid" of bromate is meant that using the test procedure described hereinafter the level of bromate, if any, is below a detectable amount. Similarly, by "essentially devoid" of bromate is meant that using the test procedure described hereinafter the presence of bromate is confirmed, but that the amount thereof is not more than 50 ppm (wt/wt).

As is known in the art, bromate is a very undesirable component of aqueous systems. For example, U.S. Pat. No. 5,922,745 points out that in 1995 the United States Environmental Protection Agency published a paper identifying some health concerns relevant to bromate formation (G. Amy, et al., *Water Supply*, 1995, 13(1), 157), and that in the same year animal carcinogenesis was linked to the presence of low levels of bromate in drinking water (J. K. Falwell, and G. O'Neill, *Water Supply*, 1995, 13(1), 29). While some prior processing achieved reductions in the amount of bromate formed when producing stabilized aqueous bromine-containing biocides, there has remained a need for still further reductions in the amount of bromate present in such biocides. Pursuant to this invention, such further reductions are possible. Furthermore, in the practice of this invention, it is deemed possible to form a concentrated aqueous biocide composition having an active bromine content of at least about 10 wt %, and preferably at least about 10.4 wt %, and e.g. in the range of about 14.5 to about 16 wt %, which is devoid or essentially devoid of bromate, and which since its inception has been devoid or essentially devoid of bromate. Thus in all stages in the production, handling, storage, transportation, and use of such compositions there is a reduced possibility of exposure to bromate. Moreover, when using a concentrated biocide solution produced pursuant to this invention in water treatment, substantial dilution occurs which further minimizes any concern about bromate. The effective biocidal amount of active bromine in the so-treated water is typically in the range of only about 0.5 to about 20 parts per million of bromine (expressed as $Br_2$) and preferably in the range of about 4 to about 10 parts per million of bromine (expressed as $Br_2$) in the aqueous medium being treated for biocidal and/or biofilm control. This in turn means that the very small amount of bromate, if any, present in the concentrated aqueous solution produced pursuant to this invention is sharply reduced by orders of magnitude in the water being treated while achieving the microbiological control for which the composition is being used.

It will be recalled that this invention provides a process in which A) an acidic aqueous solution comprising alkali metal cations, bromide anions, and sulfamate anions is formed, B) a source of alkali metal anions and a chlorine-containing bromide oxidant are fed into the solution of A) in proportions that keep the resultant aqueous medium acidic (i.e., below pH of 7) and that form an acidic product solution containing at least about 10 wt % of active bromine, and C) the pH of the product solution is raised to at least about 10, preferably by use of at least one water-soluble alkali metal base. It will thus be readily apparent that any of a variety of procedures and materials can be used in practicing such process. For example, one general procedure for preparing the concentrated biocide solutions when using sulfamic acid and an alkali metal bromide and chlorine involves, as a first step, forming a slurry of sulfamic acid in water. Typically the pH of this slurry is below 1 pH unit. The alkali metal bromide is preferably added at this point. A concentrated aqueous solution of sodium hydroxide, e.g., a 50 wt % solution, is then added until the desired pH, usually and preferably at least about 1, and more preferably at least about 2, is reached. Chlorine is then added at a rate to allow dissolution and reaction with sulfamate without forming a pool of halogen on the bottom of the reactor. An alkali metal base such as aqueous sodium hydroxide (e.g., 25 wt % to 50 wt %) is present or is co-fed to the reactor to maintain the desired pH (e.g., desirably in the range of about 1 to about 6, and more preferably in the range of about 2 to about 5). Once the addition of chlorine is finished, enough alkali metal base, usually and preferably sodium hydroxide, is added to bring the pH of the composition to the desired basic value of 10 or above. Stable solutions containing as much as 26% active bromine (11.5% on an active chlorine basis) can be prepared by use of a process of this invention.

When using an alkaline earth metal bromide and chlorine in the process, the general procedure described above except for the use of the alkaline earth metal bromide instead of the alkali metal bromide.

The same general procedure described above can be used for preparing the concentrated biocide solutions when using a salt or slurry of a salt of sulfamic acid instead of, or together with, sulfamic acid. Thus the first step typically involves forming a water solution or slurry of a sulfamic acid salt such as sodium sulfamate. From there on the general procedure is analogous.

The analytical test procedure to be used for determining the concentration, if any, of bromate in the concentrated liquid biocide composition is an ion chromatography procedure in which UV detection is employed. The equipment required for the conduct of this procedure is as follows:

a) Ion Chromatograph—Dionex DX-500 or equivalent, equipped with a UV detector and autosampler.
b) Data Acquisition and Analysis Device—VAX MULTI-CHROM or equivalent chromatography data collection and processing system.
c) Ion Chromatographic Column—Dionex IonPac AG9-HC guard column (p/n 051791) in-line with a Dionex IonPac AS9-HC column (p/n 051786).
d) Volumetric Pipettes—any standard type of suitable volume.
e) Autosampler Vials—1-mL with caps.
f) Volumetric Flasks—100-mL.
g) Syringe—5-cc plastic syringe.
h) Pretreatment Cartridge—OnGuard-H from Dionex (p/n 039596).

The chemicals required for use in the procedure are as follows:

a) Water—Deionized water with a specific resistivity of 17.8 megohm-cm or greater.
b) Sodium Carbonate—"Baker Analyzed"® reagent grade or equivalent.
c) Sodium Bromate—"Baker Analyzed"® reagent grade or equivalent.

The conditions used for the ion chromatograph are as follows:

| | |
|---|---|
| Eluent: | 4.5 millimoles (mM) sodium carbonate |
| Flow-rate | 1.0 mL/minute |
| Injection volume | 50 microliter ($\mu$L) |
| Detector Range | UV at 210 nanometers (nm) |

The eluent is prepared by dissolving 0.4770 gram of the sodium carbonate in 1 liter of the deionized water. These are mixed well and the solution is filtered through a 0.2 IC compatible filter to degas the solution. The concentrated bromate standard solution is prepared by weighing 0.1180 gram±0.001 gram of the sodium bromate into a 100-mL volumetric flask and diluting to volume with deionized water. This produces a solution containing 1,000 micrograms per milliliter of bromate. This concentrated bromate solution should be made fresh at least weekly. The bromate working standard solution is prepared by pipetting 100-microliters of the concentrated bromate standard solution into a 100-mL volumetric flask and filling the flask to volume with deionized water. The solution is mixed well, and yields a standard concentration of 1.0 microgram per milliliter of bromate.

The detailed procedure used for conducting the analysis of an aqueous solution of this invention involves the following steps:

a) Weigh 0.25 gram of the sample solution into a 100-mL volumetric flask. Fill to volume with deionized water and mix well.
b) Flush the OnGuard cartridge with 2-mL of deionized water.
c) Load 5-mL of the sample into the syringe attached to the OnGuard cartridge, pass through at a flow rate of 2 milliliters per minute, and discard the first 3 milliliters. Collect into a 1-mL autosampler vial and cap for analysis.
d) Analyze the samples, making duplicate injections, using the Ion Chromatograph instrument conditions given above.

The calculations involved in the procedure are as follows:

a) Calibration Standard: For bromate, calculate a response factor as follows: R=A/C where R is the response factor, A is the average area counts (2 injections), and C is concentration in micrograms per milliliter ($\mu$g/mL).

b) Samples: ppm bromate=A/(R×W) where A is the average area of sample peak (2 injections), R is the response factor, and W is the weight of the sample in grams.

The following example of the practice of this invention is presented for purposes of illustration and not limitation.

EXAMPLE

A 5-liter jacketed flask was charged with sulfamic acid (488 g; 5.03 mol), aqueous NaBr (968 g, 45 wt %; 4.23 mol) and 230 g of tap water. Cooling and stirring of the slurry was then begun. Aqueous NaOH (361 g, 50 wt %) was dropped in. The result was a light yellow solution with a pH of ~2. Additional water (172 g) was added to bring the liquid level up to the pH probe in the sealed position (previously, the pH probe had been inserted through an open joint), to prevent $Cl_2$ or $Br_2$ vapor escape. Aqueous NaOH (465 g, 50 wt %) was charged to the addition funnel. $Cl_2$ gas (200 g; 2.82 mol) was bubbled into the solution, which turned red. $Br_2$ vapor formation was observed and became stronger during the $Cl_2$ addition. About half the 50% NaOH was cofed with the $Cl_2$; the remainder of the NaOH was then added to bring the pH to about 10.8. During this last NaOH addition, the solution turned from clear, dark red to opaque yellow, and a precipitate formed. Although unnecessary, the solution sat overnight, after which it was filtered. The solid was analyzed by ion chromatography (IC), and found to contain 0.7 wt % sulfamate, 1.7 wt % $Br^\ominus$, and 62.1 wt % $Cl^\ominus$. Thus, the precipitate was mostly NaCl. Sodium arsenite/starch-iodine titrations found 0.9 wt % of active bromine in the solid, and 10.4 wt % of active bromine in the filtered solution.

Even though the claims hereinafter may refer to substances, components and/or ingredients in the present tense ("comprises", "is", etc.), the reference is to the substance, component or ingredient as it existed at the time just before it was first contacted, blended or mixed with one or more other substances, components and/or ingredients, or if formed in solution, as it would exist if not formed in solution, all in accordance with the present disclosure. It matters not that a substance, component or ingredient may have lost its original identity through a chemical reaction or transformation during the course of such contacting, blending, mixing, or in situ formation, if conducted in accordance with this disclosure.

Each and every patent or publication referred to in any portion of this specification is incorporated in toto into this disclosure by reference, as if fully set forth herein.

This invention is susceptible to considerable variation in its practice. Therefore the foregoing description is not intended to limit, and should not be construed as limiting, the invention to the particular exemplifications presented hereinabove. Rather, what is intended to be covered is as set forth in the ensuing claims and the equivalents thereof permitted as a matter of law.

That which is claimed is:

1. A process of producing an acidic aqueous solution containing active bromine, which process comprises:

A) forming an acidic aqueous solution comprising alkali metal cations, bromide anions, and sulfamate anions; and B) feeding into said aqueous solution a source of alkali metal cations and chlorine-containing bromide oxidant proportioned to keep the resultant aqueous medium acidic and to form an acidic product solution containing at least about 5 wt % of active bromine.

2. A process of claim 1 wherein said acidic aqueous solution of A) has a pH in the range of about 1 to about 6.

3. A process of claim 1 wherein said acidic aqueous solution of A) has a pH in the range of about 2 to about 5.

4. A process of claim 1 wherein the chlorine-containing bromide oxidant is chlorine.

5. A process of any of claim 1, 2, 3, or 4 wherein the alkali metal cations in A) and in B) are sodium cations.

6. A process of any of claim 1, 2, 3, or 4 wherein said acidic product solution contains at least about 10 wt % of active bromine.

* * * * *